(12) United States Patent
Chen

(10) Patent No.: US 6,248,753 B1
(45) Date of Patent: *Jun. 19, 2001

(54) BICYCLIC COMPOUNDS

(75) Inventor: Yuhpyng L. Chen, Waterford, CT (US)

(73) Assignee: Pfizer Inc, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/266,353

(22) Filed: Mar. 11, 1999

Related U.S. Application Data

(63) Continuation of application No. 08/967,478, filed on Nov. 11, 1997, now abandoned, which is a continuation of application No. 08/765,153, filed on Dec. 11, 1996, now abandoned, and a continuation of application No. PCT/IB95/00373, filed on May 18, 1995, which is a continuation of application No. 08/260,055, filed on Jun. 16, 1994, now abandoned.

(51) Int. Cl.$^7$ ..................... A61K 31/437; C07D 471/04; A61P 25/00
(52) U.S. Cl. ........................ 514/303; 514/252.1; 514/256; 514/275; 544/333; 544/405; 546/119; 546/120
(58) Field of Search ..................... 546/119, 120; 514/303, 256, 275, 252.1; 544/333, 405

(56) References Cited

U.S. PATENT DOCUMENTS

| | | | |
|---|---|---|---|
| 3,804,843 | * 4/1974 | Denzel | 260/294.9 |
| 3,925,388 | 12/1975 | Hoehn et al. | 260/296 H |
| 4,605,642 | 8/1986 | Rivier et al. | 514/12 |
| 5,063,245 | 11/1991 | Abreu et al. | 514/404 |

FOREIGN PATENT DOCUMENTS

| | | |
|---|---|---|
| 3145287 | 11/1981 | (DE) . |
| 0104522 | * 4/1984 | (EP) . |
| 9310359 | 11/1993 | (WO) . |
| 9310715 | 11/1993 | (WO) . |
| 9310716 | 11/1993 | (WO) . |
| 9311333 | 11/1993 | (WO) . |
| 9413677 | 6/1994 | (WO) . |
| 9510506 | 4/1995 | (WO) . |

OTHER PUBLICATIONS

M.J. Owens et al, Pharm. Rev., 43, 425 (1991).

* cited by examiner

*Primary Examiner*—Evelyn Mei Huang
(74) *Attorney, Agent, or Firm*—P. C. Richardson; P. H. Ginsburg; A. D. Joran

(57) ABSTRACT

This invention relates to compounds of the formula

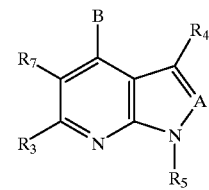

I wherein A, B, $R_3$, $R_4$, $R_5$ and $R_7$ are as defined herein, and to their use in the treatment of stress-related diseases.

13 Claims, No Drawings

BICYCLIC COMPOUNDS

This application is the continuation of 08/967,478, filed Nov. 11, 1997, abandoned, which is a continuation of 08/765,153, filed Dec. 11, 1996, abandoned, which is a continuation of PCT/IB95/00373, filed May 18, 1995, which is a continuation of 08/260,055, filed Jun. 16, 1994, abandoned.

BACKGROUND OF THE INVENTION

This invention relates to pyrazolopyridines and pyrrolopyridines, pharmaceutical compositions containing them, and methods of administering them to subjects in need of their corticotropin-releasing factor (CRF) antagonist activity.

CRF antagonists are mentioned in U.S. Pat. Nos. 4,605,642 and 5,063,245 referring to peptides and pyrazolinones, respectively. The importance of CRF antagonists is referred to in the literature, e.g., as discussed in U.S. Pat. No. 5,063,245, which is incorporated herein by reference. A recent outline of the different activities possessed by CRF antagonists is found in M. J. Owens et al., *Pharm. Rev.*, Vol. 43, pages 425 to 473 (1991), also incorporated herein by reference. Based on the research described in these and other references, CRF antagonists are believed to be effective in the treatment of a wide range of stress-related illnesses, such as depression, anxiety, headache, irritable bowel syndrome, inflammatory diseases, immune suppression, Alzheimer's disease, gastrointestinal diseases, anorexia nervosa, hemorrhagic stress, drug and alcohol withdrawal symptoms, drug addiction and infertility.

SUMMARY OF THE INVENTION

The present invention relates to a compound of the formula

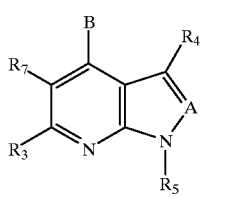

I and the pharmaceutically acceptable acid addition salts thereof, wherein

A is N or $-CR_6$;

B is $-NR_1R_2$, $-CR_1R_2R_{11}$, $-C(=CR_2R_{12})R_1$, $-NHCHR_1R_2$, $-OCHR_1R_2$, $-SCHR_1R_2$, $-CHR_2OR_{12}$, $-CHR_2SR_{12}$, $-C(S)R$, or $-C(O)R_1$;

$R_1$ is $C_1-C_6$ alkyl which may optionally be substituted with one or two substituents independently selected from the group consisting of hydroxy, fluoro, chloro, bromo, iodo, $C_1-C_4$ alkoxy, $-O-CO-(C_1-C_4$ alkyl), $-O-CO-NH(C_1-C_4$ alkyl), $-O-CO-N(C_1-C_4$ alkyl)$(C_1-C_2$ alkyl), $-NH(C_1-C_4$ alkyl), $-N(C_1-C_2$ alkyl)$(C_1-C_4$ alkyl), $-S(C_1-C_4$ alkyl), $-N(C_1-C_4$alkyl)CO$(C_1-C_4$ alkyl), $-NHCO(C_1-C_4$ alkyl), $-COO(C_1-C_4$ alkyl), $-CONH(C_1-C_4$alkyl), $-CON(C_1-C_4$ alkyl)$(C_1-C_2$ alkyl), CN, NO$_2$, $-SO(C_1-C_4$ alkyl), $-SO_2(C_1-C_4$ alkyl), and wherein any of the foregoing $C_1-C_4$ alkyl and $C_1-C_6$ alkyl groups may optionally contain one carbon-carbon double or triple bond;

$R_2$ is $C_1-C_{12}$ alkyl, aryl, $-(C_1-C_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, oxazolyl, or benzoxazolyl; or 3- to 8-membered cycloalkyl or $-(C_1-C_6$ alkylene)cycloalkyl, wherein one or two of the ring carbons of said cycloalkyl having at least 4 ring members and the cycloalkyl moiety of said $-(C_1-C_6$ alkylene)cycloalkyl having at least 4 ring members may optionally be replaced by an oxygen or sulfur atom or by N—Z wherein Z is hydrogen; or $C_1-C_4$ alkyl, and wherein each of said groups $R_2$ may optionally be substituted with from one to three substituents independently selected from chloro, fluoro, and $C_1-C_4$ alkyl, or by one substituent selected from bromo, iodo, $C_1-C_6$ alkoxy, $-O-CO-(C_1-C_6$ alkyl), $-S(C_1-C_6$ alkyl), $-COO(C_1-C_4$ alkyl), CN, NO$_2$, $-SO(C_1-C_4$ alkyl), and $-SO_2(C_1-C_4$ alkyl), and wherein said $C_1-C_{12}$ alkyl and the $C_1-C_4$ alkylene moiety of said $-(C_1-C_4$ alkylene)aryl may optionally contain one carbon-carbon double or triple bond;

or $-NR_1R_2$ may form a saturated 5- to 8-membered heterocyclic ring, or $-CHR_1R_2$ may form a saturated 5- to 8-membered carbocyclic ring, wherein each of these rings may optionally contain one or two carbon-carbon double bonds and wherein one or two of the carbon atoms of each of these rings may optionally be replaced with a sulfur or oxygen atom;

$R_3$ is $C_1-C_4$ alkyl, fluoro, chloro, bromo, iodo, $-CH_2OH$, $-CH_2OCH_3$, $-O(C_1-C_3$ alkyl), $-S(C_1-C_3$ alkyl), or $-SO_2(C_1-C_3$ alkyl), wherein said $C_1-C_3$ alkyl may optionally contain one carbon-carbon double or triple bond;

$R_4$ is hydrogen, $C_1-C_6$ alkyl, fluoro, chloro, bromo, iodo, $C_1-C_4$ alkoxy, amino, $-NHCH_3$, $-N(CH_3)_2$, $-CH_2OH$, $-CH_2OCH_3$, or $-SO_n(C_1-C_4$ alkyl), wherein n is 0, 1 or 2, cyano hydroxy, $-CO(C_1-C_4$ alkyl), $-CHO$, or $-COO(C_1-C_4$ alkyl) wherein the $C_1-C_4$ alkyl moieties in the foregoing $R_4$ groups may optionally contain one carbon-carbon double or triple bond;

$R_5$ is phenyl, naphthyl, thienyl, benzothienyl, pyridyl, pyrimidyl, benzofuranyl, pyrazinyl or benzothiazolyl, wherein each one of said groups $R_5$ may optionally be substituted with from one to three substituents independently selected from fluoro, chloro, $C_1-C_6$ alkyl and $C_1-C_6$ alkoxy, or by one substituent selected from iodo, hydroxy, bromo, formyl, cyano, nitro, amino, trifluoromethyl, $-NH(C_1-C_4$ alkyl), $-N(C_1-C_6)(C_1-C_2$ alkyl), $-COO(C_1-C_4$ alkyl), $-CO(C_1-C_4$ alkyl), $-COOH$, $-SO_2NH(C_1-C_4$ alkyl), $-SO_2N(C_1-C_4$ alkyl)$(C_1-C_2$ alkyl), $-SO_2NH_2$, $-NHSO_2(C_1-C_4$ alkyl), $-S(C_1-C_6$ alkyl) and $-SO_2(C_1-C_6$ alkyl), wherein each of said $C_1-C_4$ alkyl and $C_1-C_6$ alkyl moieties in the foregoing $R_5$ groups may optionally be substituted with one to three fluorine atoms;

$R_6$ is hydrogen, $C_1-C_4$ alkyl, fluoro, chloro, bromo, iodo, $-CH_2OH$, $-CH_2OCH_3$, or $C_1-C_4$ alkoxy;

$R_7$ is hydrogen, $C_1-C_4$ alkyl, fluoro, chloro, bromo, iodo, $-O(C_1-C_4$ alkyl), cyano, $-CH_2OH$, $-CH_2O(C_1-C_2$ alkyl), $-CO(C_1-C_2$ alkyl), or $-COO(C_1-C_2$ alkyl);

$R_{11}$ is hydrogen, hydroxy, fluoro, or methoxy; and $R_{12}$ is hydrogen or $C_1-C_4$ alkyl;

with the proviso that when A is N, then: (a) B is not unsubstituted alkyl; (b) $R_5$ is not unsubstituted phenyl; and (c) $R_3$ is not unsubstituted alkyl.

More specific embodiments of this invention relate to compounds of the formula I wherein B is —$NR_1R_2$, —$NHCHR_1R_2$, —$CR_1R_2R_{11}$, —$SCHR_1R_2$ or —$OCHR_1R_2$; $R_1$ is $C_1$–$C_4$ alkyl, which may optionally be substituted with one hydroxy, fluoro or $C_1$–$C_2$ alkoxy group and may optionally contain one carbon-carbon double or triple bond; $R_2$ is benzyl or $C_1$–$C_6$ alkyl which may optionally contain one carbon-carbon double or triple bond, wherein said $C_1$–$C_6$ alkyl or the phenyl moiety of said benzyl may optionally be substituted with fluoro, $C_1$–$C_2$ alkyl, or $C_1$–$C_2$ alkoxy; and $R_{11}$ is hydrogen or fluoro.

Other more specific embodiments of this invention relate to compounds of the formula I wherein B is tetrahydrofuranyl, tetrahydrothienyl or thiazolidinyl.

Other more specific embodiments of this invention relate to compounds of the formula I wherein: (a) $R_1$ and $R_2$ are each, independently, $C_1$–$C_4$ alkyl which may optionally be substituted with fluoro, $C_1$–$C_2$ alkyl or $C_1$–$C_2$ alkoxy and which may optionally contain one carbon-carbon double or triple bond; or (b) $R_1$ is $C_1$–$C_4$ alkyl substituted with hydroxy.

Other more specific embodiments of this invention relate to compounds of the formula I wherein: (a) $R_3$ is methyl, chloro, or methoxy; (b) $R_4$ and $R_6$ are each, independently, hydrogen, methyl, ethyl, or chloro, and $R_4$ and $R_6$ are not both hydrogen: and (c) $R_5$ is phenyl substituted by two or three substituents independently selected from fluoro, chloro, bromo, iodo, $C_1$–$C_4$ alkoxy, trifluoromethyl, $C_1$–$C_6$ alkyl which may optionally be substituted by one of hydroxy, $C_1$–$C_4$ alkoxy and fluoro and may optionally have one double or triple bond, —($C_1$–$C_4$ alkylene)O($C_1$–$C_2$ alkyl), $C_1$–$C_3$ hydroxyalkyl, hydroxy, formyl, —COO($C_1$–$C_2$ alkyl), and —C(O)($C_1$–$C_4$ alkyl).

Other more specific embodiments of this invention relate to compounds of the formula I wherein $R_3$ is methyl, ethyl halo, methoxy or thiomethyl, $R_4$ is hydrogen, $C_1$–$C_3$ alkyl, halo, thiomethyl, sulfanylmethyl, sulfonylmethyl or methoxy and $R_5$ is substituted phenyl, substituted pyridyl or substituted pyrimidyl.

Examples of specific compounds of this invention are:
butyl-[3,6-dimethyl-1-(2,4,6-trimethylphenyl)-1H-pyrazolo[3,4-b]pyridin-4-yl]-ethylamine;
3,6-dimethyl4-(tetrahydrofuran-3-yloxy)-1-(2,4,6trimethylphenyl)-1H-pyrazolo[3,4-b]pyridine
[3,6-dimethyl-1-(2,4,6-trimethylphenyl)-1H-pyrazolo[3,4,b]pyridin-4-yl]-(1-methoxymethylpropyl)-amine;
4-(1-methoxymethylpropoxy)-3,6-dimethyl-1-(2,4,6-trimethylphenyl)-1H-pyrazolo[3,4-b]pyridine;
(1-ethylpropyl)-[3,5,6-trimethyl-1-(2,4,6-trimethylphenyl)-1H-pyrazolo[3,4b]pyridin-4-yl]-amine;
4-(1-ethylpropoxy)-2,5-dimethyl-7-(2,4,6-trimethylphenyl)-7H-pyrrolo[2,3-b]pyridine;
4-(1-ethylpropoxy)-2,5,6-trimethyl-7-(2,4,6-trimethylphenyl)-7H-pyrrolo[2,3-b]pyridine; and
4-(1-ethylpropoxy)-2,5-dimethyl-7-(2,6-dimethyl4-bromophenyl)-7H-pyrrolo[2,3-b]pyridine.

Compounds of the formula I wherein $R_5$ is substituted with one substituent selected from hydroxymethyl, —$CH_2O$($C_1$–$C_6$ alkyl) and $CH_2OCF_3$ are also CRF antagonists and are useful in the treatment of the disorders enumerated in the following two paragraphs.

The invention also relates to a pharmaceutical composition for the treatment of (a) a disorder the treatment of which can be effected or facilitated by antagonizing CRF, including but not limited to disorders induced or facilitated by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer; irritable bowel syndrome, Crohn's disease; spastic colon; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies and addictions (e.g., dependencies on alcohol, cocaine, heroin, benzodiazepines, or other drugs); drug and alcohol withdrawal symptoms; stress-induced psychotic episodes; euthyroid sick syndrome; syndrome of inappropriate antidiuretic hormone (ADH); obesity; infertility; head traumas; spinal cord trauma; ischemic neuronal damage e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; and hypoglycemia in a mammal, including a human, comprising an amount of a compound of the formula I, or a pharmaceutically acceptable salt thereof, that is effective in the treatment of such disorder, and a pharmaceutically acceptable carrier.

The invention further includes a method for the treatment of (a) a disorder the treatment of which can be effected or facilitated by antagonizing CRF, including but not limited to disorders induced or facilitator by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer; irritable bowel syndrome; Crohn's disease; spastic colon; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; stress-induced psychotic episodes; euthyroid sick syndrome; syndrome of inappropriate antidiuretic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.q., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimers type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; and hypoglycemia in a mammal, including a human, comprising administering to a subject in need of said treatment an amount of a compound of the formula I or a pharmaceutically acceptable salt thereof, that is effective in treating such disorder.

The invention further includes intermediate compounds of the formula

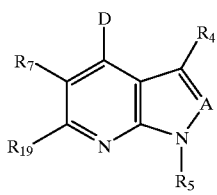

II wherein D is chloro, hydroxy or cyano, $R_{19}$ is methyl, ethyl or chloro, and A, $R_4$, $R_5$ and $R_7$ are as defined above with reference to formula I.

DETAILED DESCRIPTION OF THE INVENTION

As used herein, unless otherwise indicated, the term "$C_1$–$C_6$ alkyl", refers to a straight or branched chain alkyl of one to six carbon atoms, such as methyl, ethyl, isopropyl, t-butyl or hexyl.

Whenever reference is made herein to 3- to 8-membered cycloalkyl containing one or two of O, S or N—Z, it is understood that the oxygen and sulfur ring atoms are not adjacent to each other. An example of a six-membered cycloalkyl having O and N is morpholinyl.

Whenever $R_2$ or $R_5$ is a heterocyclic group, the point of attachment of such group is through a carbon atom.

Whenever reference is made herein to $C_1$–$C_4$ alkyl or $C_1$–$C_6$ alkyl which "may contain one double or triple bond" in the definitions of $R_1$, $R_2$ and $R_3$, it is understood that at least two carbons are present in the alkyl group.

As used herein, unless otherwise indicated, the terms "halo", "halogen" and "Hal" refer to fluoro, chloro, bromo or iodo.

Compounds of the formulae I and II may contain chiral centers and therefore many exist in different enantiomeric forms. This invention relates to all optical isomers and stereoisomers of compounds of the formulae I and II and to mixtures thereof.

Compounds of the formula I wherein B is —$NR_1R_2$, —$NHCHR_1R_2$, —$OCHR_1R_2$ or —$SCHR_1R_2$, and $R_3$ is $C_1$–$C_4$ alkyl or chloro may be prepared by reaction of a compound of the formula II wherein D is Cl, and $R_4$, $R_5$, $R_7$ and A are as defined above with reference to formula I, with a compound of the formula BH wherein B is as defined immediately above or with a compound of the formula $R_1NH_2$. The reaction is carried out in a solvent in the presence of a base at a temperature between about room temperature and about 230° C., with or without an organohalide such as copper bromide, iodide or chloride, or magnesium bromide, or with or without an acid catalyst such as p-toluene sulfonic acid. Suitable solvents are organic solvents such as tetrahydrofuran (THF), acetonitrile, dimethylsulfoxide (DMSO), acetone, $C_2$–$C_5$ alkyl alcohol, chloroform, benzene, xylene, dioxane, toluene, sulfolane, pyridine, or 1-methyl-2-pyrrolidinone. The solvent is preferably dimethylsulfoxide or 1-methyl-2-pyrrolidinone.

When B in the desired compound of formula I is —$NR_1R_1$ or —$NHCHR_1R_2$, an excess of BH may be used as a reagent and a base. Bases other than BH, such as potassium carbonate and tri-($C_1$–$C_6$)alkylamine may also be used. This reaction is generally carried out at a temperature from about 75° to about 230° C. An organohalide such as copper bromide may be added to facilitate the reaction. When the reaction is very inert, compounds of the formula I wherein B is —$NR_1R_2$ or —$NHCHR_1R_2$ can be prepared by a two step reaction, as described below. Reaction of compounds of formula II with an excess of $R_1NH_2$ or $NH_3$ or an equivalent $NH_3$ recursor (e.g., $NaN_3$, $nBu_4N^+N_3^-$ or $NH_2OH$) at temperature from about 75° C. to about 250° C. and at a pressure from about 0 to about 300 psi, in an appropriate solvent as described above, yields compounds of formula I wherein B is —$NHR_1$, —$NH_2$, —$NH_2OH$ or —$N_3$. Conversion of compounds of formula I wherein B is —$N_3$ or —$NH_2OH$ into the corresponding compounds of formula I wherein B is —$NH_2$ can be accomplished by methods known in the art such as hydrogenation or reduction. Alkylation of compounds of formula I wherein B is —$NHR_1$ or —$NH_2$ with an appropriate alkyl halide in the presence of an appropriate base such as lithium or sodium bistrimethylsilylamide or lithium or sodium diisopropylamide or n-butyllithium or potassium t-butoxide, in an appropriate solvent such as THF, dioxane or methylene chloride, will give the corresponding compounds of formula I wherein B is —$NR_1R_2$. Alternatively, acylation of compounds of formula I wherein B is —$NHR_1$ or —$NH_2$, followed by reduction with a borohydride (e.g., sodium borohydride) will give compounds of formula I wherein B is —$NR_1R_2$.

Alternatively, when the reaction of BH and the appropriate compound of formula II is very inert, acidic conditions obtained with p-toluenesulfonic acid or phenol or its derivatives may be used.

When B is —$OCHR_1R_2$ or —$SCHR_1R_2$, a base which is capable of deprotonating BH may be used, such as an alkali metal hydride such as sodium or potassium hydride, or an organometallic base such as sodium diisopropylamide, sodium bis(trimethylsilyl)amide, lithium diisopropylamide, lithium or sodium bis(trimethylsilyl)amide or n-butyllithium. The solvent is preferably tetrahydrofuran, dimethylsulfoxide, methylene chloride, toluene, sulfolane or 1-methyl-2-pyrrolidinone, and the reaction is typically carried out between about room temperature and 180° C., preferably between about 50° C. and about 130° C.

The compounds of formula I wherein B is —$CR_1R_2R_{11}$, —$C(C=CR_2R_{12})R_1$, —$CHR_2OR_{12}$, —$CHR_2SR_{12}$, —$C(S)R_1$ or —$C(O)R_1$, and $R_3$ is chloro or ($C_1$–$C_4$)alkyl may be prepared as depicted in Scheme I.

SCHEME 1

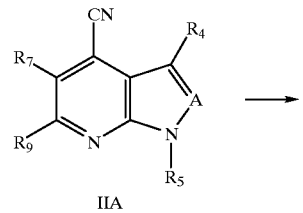

IIA

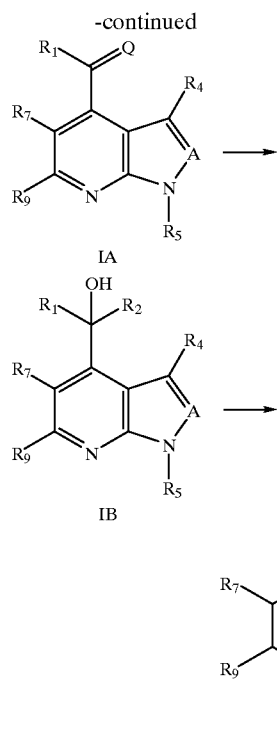

IA

IB

IC

Compounds of the formula II wherein D is cyano, $R_4$, $R_5$ and $R_7$ are as defined above and $R_9$ is $(C_1$-$C_4)$alkyl or chloro (hereinafter referred to as compounds of the formula IIA), may be prepared by reacting the corresponding compounds of the formula II wherein D is chloro with potassium cyanide or copper cyanide with or without a sodium p-toluenesulfonate or sodium methanesulfonate catalyst in dimethylsulfoxide or N,N-dimethylformamide. These compounds (IIA) are then reacted with a Grignard reagent containing the group $R_1$, as defined above, to form compounds of the formula IA wherein Q is O. Compounds of the formula IA wherein Q is S may be prepared by reacting the corresponding compounds of formula IA wherein Q is O with Lawesson's Reagent or by another method well known to those skilled in the art. Reaction of the compounds of formula IA wherein Q is O with a Grignard reagent containing group $R_2$, as defined above, provides the corresponding compounds of formula IB. The corresponding compounds of the formula IC wherein B is —$CR_1R_2R_{11}$ or —$C(C$=$CR_2R_{12})R_1$ may be prepared by conventional methods well known to those skilled in the art. Thus, reaction of a compound of the formula IB with an acid, such as concentrated sulfuric acid in acetic acid, or Burgess inner salt, such as (carboxysulfamoyl)triethylammonium hydroxide methyl ester, gives a compound of the formula IC wherein B is —$C(=CR_2R_{12})R_1$. Hydrogenation of a compound of the formula IC wherein B is —$C(=CR_2R_{12})R_1$ using a palladium/carbon or platinum oxide catalyst gives a compound of the formula IC wherein B is —$CHR_1R_2$. Reaction of compound of the formula IB with diethylaminosulfur trifluoride or triphenylphosphine together with carbon tetrachloride, carbontetrabromide, or iodine affords a compound of the formula IC wherein B is —$CR_1R_2F$ or —$CR_1R_2$Hal, respectively. Reduction of a compound of the formula IA with sodium borohydride gives a compound of the formula I wherein B is —$CHR_1OH$. Alkylation of this —$CHR_1OH$ group with an alkyl halide such as alkyl iodide in the presence of a base such as sodium hydride at room temperature affords a compound of the formula I wherein B is —$CHR_2OR_1$.

Compounds of the formula II wherein A is N, D is OH and $R_9$ is $C_1$-$C_4$ alkyl may be prepared, as shown in Scheme 2, by reacting a compound of the formula IV with a compound of the formula III in the presence of an acid catalyst, such as p-toluenesulfonic acid, HCl, or $H_2SO_4$, in an appropriate solvent such as toluene, benzene or xylene, under Dean-Stark trap conditions at a temperature between about 60 and 150° C., preferably at reflux. Similarly, when ClC(O)CH($R_7$)COO($C_1$-$C_4$ alkyl) is used instead of a compound of the formula III, the corresponding compound wherein $R_9$ is OH is obtained. Conversion of compounds wherein $R_9$ is OH to Cl can be accomplished by reaction with a chlorinating agent such as $POCl_3$ in the presence of a base such as N-diethylaniline. Compounds of the formula IV can be obtained by acid hydrolysis of the corresponding compounds of the formula V at the reflux temperature. Examples of suitable acids are 85% phosphoric acid, aqueous HCl and aqueous $H_2SO_4$. Compounds of the formula V may be prepared by the methods disclosed in copending patent application Serial No. PCT/US93/11333, which designates the United States and was filed on Nov. 26, 1993, or by procedures known to those skilled in the art. World Patent Application PCT/US 93/11333 is incorporated herein by reference in its entirety.

SCHEME 2

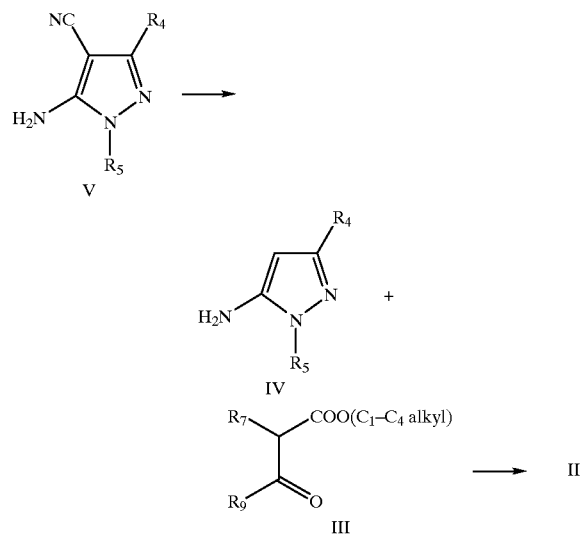

Compounds of the formula II wherein A is —$CR_6$ and $R_9$ is $C_1$-$C_4$ alkyl may be prepared as shown in Scheme 3. Compounds of the formula VII wherein $R_7$ is —COOR, CN, or —CO—($C_1$-$C_2$ alkyl), may be prepared by heating compounds of the formula VI with $R_9C(O)CHR_7$ wherein $R^9$ is chloro or $(C_1$-$C_4)$alkyl, in an appropriate solvent such as toluene, xylene, or benzene, in the presence of acid catalyst such as p-toluenesulfonic acid, sulfuric acid or gaseous HCl at a temperature between about 80° C. and 150° C., preferably at the reflux temperature under a Dean-stark trap to remove water, followed by cyclization. The cyclization may be performed under acidic conditions such as 85% to 100% phosphoric acid or sulfuric acid at reflux, or under basic conditions such as sodium ethoxide in ethanol or sodium hydride (NaH) in THF or DMSO, at a temperature between about 25° C. and 100° C. Conversion of compounds of formula VII to compounds of the formula IIB wherein D is OH may be accomplished by methods well known in the art.

Compounds of the formula I wherein $R_7$ is other than —COOR, —COR or CN may be prepared through an intermediate of the formula IIB or a compound of the formula ID, wherein $R_7$ is —COOR, —COR or CN, as shown in Scheme 3, by conversion of the $R_7$ group to other $R_7$ groups using general organic methods known in the art. For example, hydrolysis of a compound wherein $R_7$ is an ester with a base (e.g., lithium hydroxide in 1:1 water:dioxane or 1:1 water:methanol or aqueous LiOH or NaOH) at a temperature between about 80° C. and 100° C., followed by quenching with an acid and heating at the reflux temperature to accomplish decarboxylation gives the corresponding compound of the formula ID wherein $R_7$ is H. Reduction of compounds wherein $R_7$ is an ester group with a reducing agent such as $LiAlH_4$ or diisobutylaluminum hydride affords the corresponding compounds wherein $R_7$ is $CH_2OH$ or CHO. Alkylation of the $CH_2OH$ group with a base such as NaH, sodium alkoxide or organolithium agents, followed by alkylation with methyl iodide or ethyl iodide gives the compounds of the formula ID wherein $R_7$ is —$CH_2OCH_3$ or —$CH_2OC_2H_5$. Grignard reaction of —$CO_2CH_3$, —$CO_2C_2H_5$, —$COCH_3$ or —$COC_2H_5$, followed by elimination and hydrogenation gives compounds of the formula ID wherein $R_7$ is an alkyl group. Compounds of the formula IIB or ID wherein $R_7$ is $CH_2OH$ may be converted into the corresponding compounds wherein $R_7$ is $CH_2Cl$ or $CH_2F$ as follows. Reaction of $HCOCH_3$ with a peracid, followed by hydrolysis gives the corresponding compound wherein $R_7$ is hydroxy. Reaction of the hydroxy group with a base, followed by quenching with a $C_1$–$C_4$ alkyl halide gives the corresponding compound wherein $R_7$ is —$O(C_1$–$C_4$ alkyl). Conversion of compounds wherein $R_7$ is hydroxy into those wherein $R_7$ is halo may be performed by conventional methods. In the above synthetic sequence, a protecting or deprotecting method may be required to achieve the desired compounds.

An alternative method for preparing compounds of the formula IIB wherein D is hydroxy, chloro or cyano is shown below in Scheme 4.

SCHEME 4

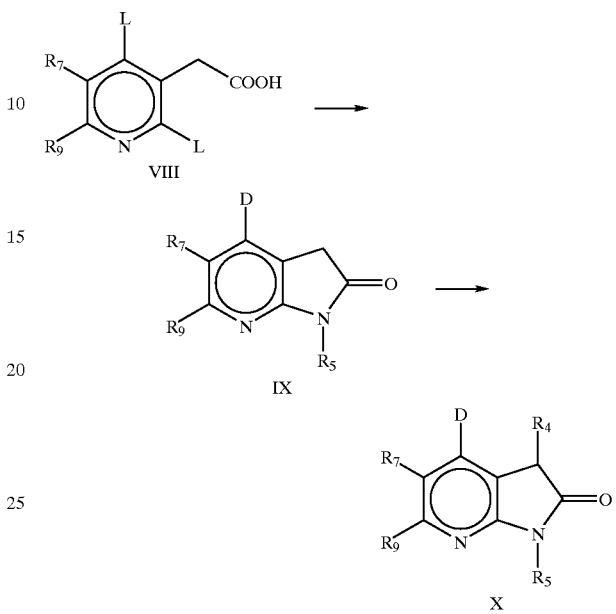

Compounds of the formula VIII wherein L and L' are suitable leaving groups, such as chloro, bromo, mesyl, tosyl or methoxy, may be converted into a compound of the formula IX wherein D is hydroxy or L' by reaction with an amine of the formula $R_5NH_2$ in the presence of a catalytic amount of an acid such as p-toluenesulfonic acid or sulfuric acid or a base which is capable of deprotonating $R_5NH_2$ such as n-butyllithium or an organohalide such as copper bromide, chloride or iodide, or magnesium bromide. The

SCHEME 3

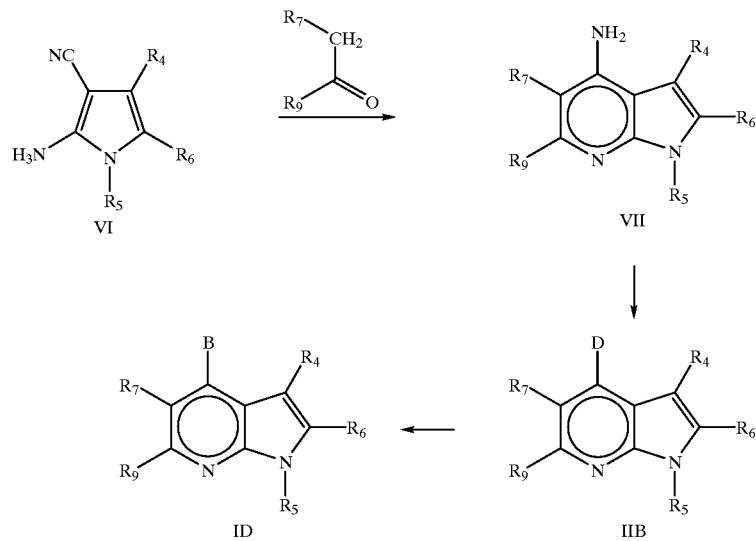

reaction may be carried out with or without a suitable solvent such as an alcohol (e.g., pentanol), DMSO, sulfolane or dioxane. Alkylation of the compounds of formula IX to introduce $R_4$ may be carried out by conventional methods. Preferably, the process is carried out by first adding a base, such as sodium or potassium hydride, to a compound of the formula IX contained in an inert solvent, such as an ether, e.g., diethylether, THF or dioxane, or a polar aprotic solvent such as DMSO, under an inert atmosphere, e.g., nitrogen, followed by addition of a compound of the formula $R_4L$ wherein L is as defined above. The reaction temperature is preferably between about 0° C and about 25° C. When $R_4$ is halogen, $R_4L$ is a halogenating agent such as bromine, chlorine, iodine, diethylaminosulfurtrifluoride or N-bromosuccinimide. Compounds of the formula X wherein $R_4$ is thiophenyl, which may be prepared by reacting compounds of formula IX with phenyl-S—$SO_n$-phenyl wherein n is 0, 1 or 2, may be converted into compounds of the formula X wherein $R_4$ is $C_1$–$C_6$ alkyl by reaction with $C_1$–$C_6$ alkyl iodide, followed by reduction of the thiophenyl group with Raney nickel or trimethylsilylchloride (TMSCl) with zinc to provide a selective monosubstituted compound of the formula X.

Compounds of the formula IIB wherein $R_6$ is hydrogen may be formed from compounds of the formula X by reduction, e.g., with lithium aluminum hydride or diisobutyl aluminum hydride, followed by elimination or dehydrogenation. Reaction of compounds of the formula X by organometal addition, e.g., by reaction with dialkyl zinc, dialkylaluminum hydride or Grignard reagents containing group $R_6$, followed by hydrolysis or dehydrogenation, provides compounds of the formula IIB wherein $R_6$ is other than hydrogen. Reaction of compounds of the formula X with a halogenating agent such as $POCl_3$, $SOCl_2$, $PCl_3$, or triphenylphosphine with iodine in the presence of a base such as pyridine gives compounds of the formula IIB wherein $R_6$ is halogen. Reaction of compounds of the formula X with a base such as a trialkylamine, sodium hydride or pyridine, followed by quenching with a dialkyl sulfate or a $C_1$–$C_4$ alkyl-trifluoromethanesulfonate in an appropriate solvent such as hexamethylphosphoramide, affords compounds of the formula IIB wherein $R_6$ is —O($C_1$–$C_4$) alkyl.

Compounds of the formula I, wherein B is as defined with reference to formula I and $R_3$ is other than chloro or ($C_1$–$C_4$)alkyl, may be prepared by reacting a compound of the formula I wherein $R_3$ is chloro with a nucleophile of the formula $R_{10}H$, wherein $R_{10}$ is defined as $R_3$ except that it cannot be chloro or ($C_1$–$C_4$)alkyl, with or without an organic or inorganic base. Suitable bases include sodium and sodium hydride when $R_{10}H$ is an alkanol or an alkane thiol, and weaker bases such as potassium carbonate or triethylamine when $R_{10}H$ is an amine. Compounds of the formula I wherein $R_{10}$ is fluoro may be prepared from the corresponding compounds wherein $R_9$ is chloro by reaction with tetrabutylammonium fluoride. Suitable solvents for this reaction include dimethylsulfoxide, tetrahydrofuran and methylene chloride. The solvent is preferably tetrahydrofuran.

The acid addition salts are prepared in a conventional manner by treating a solution or suspension of the free base of a compound of the formula I with one chemical equivalent of a pharmaceutically acceptable acid. Conventional concentration or crystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The active compounds of this invention (compounds of the formula I and their pharmaceutically acceptable salts) may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the novel compounds of formula I and pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of an active compound of this invention in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosage for the active compounds of this invention depends on the intended route of administration and other factors such as age and weight of the patient, as generally known to a physician. The dosage also depends on the illness to be treated. The daily dosage for stress-induced illnesses will generally range from about 0.1 to 50 mg/kg of the body weight of the patient to be treated, for treatment of inflammatory diseases about 0.1 to about 50 mg/kg will be needed, for Alzheimer's disease, about 0.1 to about 50 mg/kg, for gastrointestinal diseases about 0.1 to about 50 mg/kg, for anorexia nervosa about 0.1 to about 50 mg/kg, for hemorrhagic stress about 0.1 to about 50 mg/kg, for drug and alcohol withdrawal symptoms, about 0.1 to about 50 mg/kg.

The active compounds of this invention will generally be administered from one to three times per day (i.e., from one to three doses per day), with each dose containing from about 0.1 to about 100 mg/kg body weight, although variations will necessarily occur depending upon the weight and condition of the subject being treated, the nature and severity of the disorder for which the subject is being treated and the particular route of administration chosen. However, a dosage level that is in the range of about 1.0 mg to about 50 mg per kg of body weight per individual dose will most desirably be employed. Variations may nevertheless occur depending upon the species of mammal being treated and the individual subject's response to said medicament, as well as on the type of pharmaceutical formulation chosen and the time period and interval at which such administration is carried out.

Methods for determining the CRF antagonist activity of compounds of the formula I and their pharmaceutically acceptable salts are described in *Endocrinology*, 116, 1653–1659 (1985) and *Peptides*, 10, 179–188 (1985). The binding activities for the compound of formula I, expressed as $IC_{50}$ values, generally range from 0.5 nanomolar to about 10 micromolar.

The following Examples illustrate the preparation of the compounds of the present invention. Melting points are uncorrected. NMR data are reported in parts per million ($\delta$) and are referenced to the deuterium lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to dimethylformamide. Chromatography refers to column chromatography performed using 32–63 $\mu$m silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure implies the use of a rotary evaporator.

EXAMPLE 1

(1-Ethylpropyl)-[3,5,6-trimethyl-1-(2,4, 6trimethylphenyl)-1H-pyrazolo[3,4-b]pyridin-4-yl]-amine A mixture of 4-chloro-3,5,6-trimethyl-1-(2,4,6-trimethylphenyl)-1H-pyrazolo[3,4-b]pyridin (227 mg, 0.72 mmol), p-TsOH (124 mg) and ethylpropylamine (0.5 ml) in 1 ml of dimethylsulfoxide (DMSO) was heated at reflux for 4 hours (thin layer chromatography showed no reaction). Copper bromide (40 mg) was added and the reaction was heated for an additional 15 hours at reflux. The reaction mixture was quenched with saturated ammonium chloride and extracted with ethyl acetate (EtOAc). The organic layer was washed with brine, dried and concentrated to give a brown oil. The oil residue was purified through silica gel column chromatography using chloroform ($CHCl_3$) and hexane in a ratio of 8:3 as eluent to give the title compound as a colorless oil. $^1$H NMR ($CDCl_3$) 6.92 (s, 2H), 3.97 (d, 1H, NH), 3.56 (brs, 1H, OH), 2.70 (s, 3H), 2.43 (s, 3H), 2.29 (s, 3H), 2.18 (s, 3H), 1.89 (s, 6H), 1.4~1.7 (m, 4H), 0.94 (t, 6H) ppm. The compound was prepared as the corresponding HCl salt as an off-white crystals after recrystallization from a solvent mixture of ethyl ether and ethyl acetate, mp 201–205° C.

EXAMPLE 2

Butyl-[3,6dimethyl-1-(2,4,6-trimethylphenyl)-1H-pyrazolo[3,4-b]pyridin-4-yl]ethylamine A mixture of 4-chloro-3,6-dimethyl-1-(2,4,6-trimethylphenyl)-1H-pyrazolo[3,4-b]pyridine (98 mg, 0.33 mmol), N-butylethylamine (1 ml) in DMSO (2 ml) was heated in an oil bath at 175–180° C. for 20 hours. The reaction mixture was quenched with saturated ammonium chloride and extracted with EtOAc. The organic layer was washed with brine, dried, and concentrated to give a brown oil. The oil residue was purified through silica gel column chromatography using EtOAc/Hexane in a ratio of 1/9 as eluent to give a colorless oil. $^1$H NMR ($CDCl_3$) 6.92 (s, 2H), 6.29 (s, 1H), 3.42 (q, 2H), 3.27 (t, 2H), 2.65 (s, 3H), 2.44 (s, 3H), 2.30 (s, 3H), 1.91 (s, 6H), 1.57 (m, 2H), 1.33 (m, 2H), 1.13 (t, 3H), 0.90 (t, 3H) ppm. IR (neat) 2960, 2920, 1570 cm−1. High MS, calc. 364.2627, found 364.26306.

EXAMPLE 3

2-[3,6-Dimethyl-1-(2,4,6-trimethylphenyl)-1H-pyrazolo[3,4,-b]pyridin-4-ylamino]-butan-1-ol A mixture of 4-chloro-3,6-dimethyl-1-(2,4,6-trimethylphenyl)-1H-pyrazolo[3,4-b]pyridine (380 mg, 1.27 mmol), (S)-2-amino-1-butanol (0.9 ml) in DMSO (2 ml) was heated in an oil bath at 190° C. for 20 hours. The reaction mixture was quenched with water and extracted with EtOAc. The organic layer was washed with brine, dried, and concentrated to give a brown oil. The oil residue was purified through silica gel column chromatography using EtOAc/Hexane=1/9 as eluent to give 113 mg of the title compound as a yellow oil. 1H NMR ($CDCl_3$): 6.9 (s, 2H), 5.95 (s, 1H), 4.94 (d, 1H), 3.70 (m, 2H), 3.52 (m, 1H), 2.62 (s, 3H), 2.40 (s, 3H), 2.28 (s, 3H), 1.92 (s 3H), 2.6–2.8 (m, 2H), 1.0 (t, 3H) ppm.

EXAMPLE 4

2-[3,6-Dimethyl-1-(2,4,6-trimethylphenyl)-1-H-pyrazolo[3,4-b]pyridin-4-ylamino]-butan-1-ol and 3, 6-Dimethyl4-phenoxy-1-(2,4,6-trimethylphenyl)-1H-pyrazolo[3,4-b]pyridine A mixture of 4-chloro-3,6-dimethyl-1-(2,4,6-trimethylphenyl)-1H-pyrazolo[3,4-b]pyridine (300 mg, 1 mmol), (S)-2-amino-1-butanol (107 mg, 1.2 mmol) and phenol (188 mg, 2 mmol) was heated in 190° C. oil bath for 15 hours. The mixture was cooled, quenched with 2 N sodium hydroxide and extracted with chloroform. The organic layer was separated and neutralized with 2 N hydrochloride and water. The organic layer was dried and concentrated to give an oil residue. The residue was purified through silica gel column chromatography using chloroform as eluent to give 157 mg of starting material, and 52 mg of 3,6-dimethyl-4-phenoxy-1-(2,4,6-trimethylphenyl)-1H-pyrazolo-[3,4-b]pyridine as beige crystals. 1H NMR ($CDCl_3$): 7.1–7.45 (m, 5H), 6.95 (s, 2H), 6.06 (s, 1H), 2.71 (s, 3H), 2.38 (s, 3H), 2.29 (S, 3H), 1.94 (s, 6H) ppm; and 30 mg of 2-[3,6-dimethyl-1-(2,4,6-trimethylphenyl)-1-H-pyrazolo[3,4-b]pyridin4-ylamino]-butan-1-olasa yellow glass.

EXAMPLE 5

[3,6-Dimethyl-1-(2,4,6-trimethyphenyl)-1H-pyrazolo[3,4-b]pyridin-4-yl]-(1-methoxymethyl-propyl)-amine A solution of 2-[3,6dimethyl-1-(2,4,6-trimethylphenyl)-1H-pyrazolo[3,4-b]pyridin-4-ylamino]-butan-1-ol (69 mg, 0.196 mmol) in 1 ml of dry tetrahydrofuran was treated with 60% sodium hydride oil (28 mg, 0.7 mmol). After stirring for 3 minutes, methyliodide (0.3 ml) was added and the mixture was stirred at room temperature for 1.5 hours. The mixture was quenched with water and extracted with ether. The organic layer was washed with water, dried and concentrated to give 61 mg of crude material. The residue was purified through silica gel column chromatography using chloroform as eluent to give 43 mg of the title compound in yellow glass form. 1H NMR (CDCl$_3$): 6.91 (s, 2H), 6.00 (s, 1H), 5.05 (d, 1H), 3.4–3.6 (m, 2h), 3.41 (s, 3H), 2.66 (s, 3H), 2.28 (s, 3H), 1.92 (s, 3H), 1.91 (s, 3H), 1.6–1.8 (m, 2H), 1.05 (t, 3H), ppm; IR (CHCl$_3$) 2920, 1586 cm–1; High MS calc. 366.2413, found 3.66.24516. The glass form was converted to the corresponding HCl salt form as a yellow solid.

EXAMPLE 6

4-(1-Methoxymethyl-propoxy)-3,6-dimethyl-1-(2,4,6-trimethylphenyl)-1H-pyrazolo[3,4-b]pyridine Sodium hydride (60% in oil, 94 mg, 1.33 mmol) was washed with hexane and suspended in 2 ml of tetrahydrofuran (THF). 1-Methoxy-2-butanol (0.7 ml) was added and stirred at room temperature for 5 minutes. A solution of 4chloro3,6dimethyl-1-(2,4,6-trimethylphenyl)-1H-pyrazolo[3,4-b]pyridine (200 mg, 0.665 mmol) in 1 ml of THF was added and the resulting mixture was heated at reflux for 15 hours. The mixture was quenched with water and extracted with EtOAc. The organic layer was dried and concentrated to give 201 mg of crude product as a yellow solid. The solid was purified through silica gel column chromatography using 1% methanol in chloroform as eluent to give 175 mg of off-white crystals, mp 108–108° C.; IR (KBr) 2900, 1600, 1580 cm–1; high MS, calc. 367.2253, found, 367.22754; 1H NMR (CDCl$_3$): 6.93 (s, 2H), 6.34 (s, 1H), 4.59 (m, 1H), 3.64 (2 sets ABq, 2H), 3.41 (s, 3H), 2.64 (s, 3H), 2.48 (s, 3H), 2.29 (s, 3H), 1.91 (s, 3H), 1.89 (s, 3H) 1.7–1.9 (m, 2H), 1.04 (t, 3H) ppm.

EXAMPLE 7

3,6-Dimethyl-4-(tetrahydrofuran-3-yloxy)-1-(2,4,6-trimethylphenyl)-1H-pyrazolo[3,4-b]pyridine Sodium hydride (60% in oil, 176 mg, 4.4 mmol) was washed with hexane and suspended in 2 ml of tetrahydrofuran. 3-Hydroxytetrahydrofuran (1 ml) was added and stirred at room temperature for 5 minutes. A solution of 4-chloro-3,6-dimethyl-1-(2,4,6-trimethylphenyl)-1H-pyrazolo[3,4-b]pyridine (200 mg, 0.665 mmol) in 1 ml of THF was added and the resulting mixture was heated at reflux for 8 hours. The mixture was quenched with water and extracted with EtOAc. The organic layer was dried and concentrated to give 334 mg of crude product. The crude material was purified through silica gel column chromatography using 1% methanol in chloroform as eluent to give 127 mg of a beige solid, mp 117–119° C.; IR(KBr) 2950, 1600, 1580 cm–1; high MS, calc. 351.1941, found, 351.19386; 1H NMR (CDCl$_3$): 6.90 (s, 2H), 6.15 (s, 1H), 5.07 (m, 1H), 3.9–4.05 (m, 4H), 2.6 (s, 3H), 2.47 (s, 3H), 2.38 (s, 3H), 2.2–2.3 (m, 2H), 1.98 (s, 3H), 1.96 (s, 3H) ppm.

EXAMPLE 8

1-[3,6-Dimethyl-1-(2,4,6-trimethylphenyl)-1H-pyrazolo[3,4-b]pyridin-4-yl]propan-1-one A solution of 3,6-dimethyl-1-(2,4,6-trimethylphenyl)-1H-pyrazolo[3,4-b]pyridine-4-carbonitrile (200 mg, 0.690 mmol) in 1 ml benzene was added to a solution of ethylmagnesiumbromide (1M, 1.5 ml, 1.5 mmol) in 4 ml benzene at room temperature after stirring at room temperature for 10 minutes. The reaction mixture was quenched with 2 N hydrogen chloride and stirred for 5 minutes, worked up with water, neutralized with 2 N sodium hydroxide, and extracted with EtOAc. The organic layer was dried and concentrated to give a yellow oil. The oil was purified through silica gel column chromatography using 5% EtOAc in hexane as eluent to give 118 mg of the title compound as a yellow solid, mp 117–118° C.; R (KBr) 2980, 2923, 1691, 1573, 1502.

What is claimed is:
1. A compound of the formula

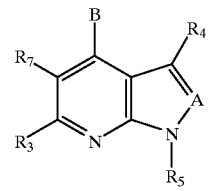

and the pharmaceutically acceptable acid addition salts thereof, wherein

A is N;

B is —NR$_1$R$_2$, —CR$_1$R$_2$R$_{11}$, —C(=CR$_2$R$_{12}$)R$_1$, —NHCHR$_1$R$_2$, —OCHR$_1$R$_2$, —SCHR$_1$R$_2$, —CHR$_2$OR$_{12}$, —CHR$_2$SR$_{12}$, —C(S)R$_1$ or —C(O)R$_1$;

R$_1$ is C$_1$–C$_6$ alkyl which may optionally be substituted with one or two substituents independently selected from the group consisting of hydroxy, fluoro, chloro, bromo, iodo, C$_1$–C$_4$ alkoxy, —O—CO—(C$_1$–C$_4$ alkyl), —O—CO—NH(C$_1$–C$_4$ alkyl), —O—CO—N(C$_1$–C$_4$ alkyl)(C$_1$–C$_2$ alkyl), —NH(C$_1$–C$_4$ alkyl), —N(C$_1$–C$_2$ alkyl)(C$_1$–C$_4$ alkyl), —S(C$_1$–C$_4$ alkyl), —N(C$_1$–C$_4$alkyl)CO(C$_1$–C$_4$ alkyl), —NHCO(C$_1$–C$_4$ alkyl), —COO(C$_1$–C$_4$ alkyl), —CONH(C$_1$–C$_4$ alkyl), —CON(C$_1$–C$_4$ alkyl)(C$_1$–C$_2$ alkyl), CN, NO$_2$, —SO(C$_1$–C$_4$ alkyl), —SO$_2$(C$_1$–C$_4$ alkyl), and wherein any of the foregoing C$_1$–C$_4$ alkyl and C$_1$–C$_6$ alkyl groups may optionally contain one carbon-carbon double or triple bond;

R$_2$ is C$_1$–C$_{12}$, optionally substituted with from one to three substituents independently selected from chloro, fluoro, and C$_1$–C$_4$ alkyl, or by one substituent selected from bromo, iodo, C$_1$–C$_6$ alkoxy, —O—CO—(C$_1$–C$_6$ alkyl), —S(C$_1$–C$_6$ alkyl), —COO(C$_1$–C$_4$ alkyl), CN, NO$_2$, —SO(C$_1$–C$_4$ alkyl), and —SO$_2$(C$_1$–C$_4$ alkyl);

or —NR$_1$R$_2$ may form a saturated 5- to 8-membered heterocyclic ring, or —CHR$_1$R$_2$ may form a saturated 5- to 8-membered carbocyclic ring, wherein each of these rings may optionally contain one or two carbon-carbon double bonds and wherein one or two of the carbon atoms of each of these rings may optionally be replaced with a sulfur or oxygen atom;

R$_3$ is C$_1$–C$_4$ alkyl, fluoro, chloro, bromo, iodo, —CH$_2$OH, —CH$_2$OCH$_3$, —O(C$_1$–C$_3$ alkyl), —S(C$_1$–C$_3$ alkyl), or —SO$_2$(C$_1$–C$_3$ alkyl), wherein said C$_1$–C$_3$ alkyl may optionally contain one carbon-carbon double or triple bond;

R$_4$ is hydrogen, C$_1$–C$_6$ alkyl, fluoro, chloro, bromo, iodo, C$_1$–C$_4$ alkoxy, amino, —NHCH$_3$, —N(CH$_3$)$_2$, —CH$_2$OH, —CH$_2$OCH$_3$, or —SO$_n$(C$_1$–C$_4$ alkyl), wherein n is 0, 1 or 2, cyano, hydroxy, —CO(C$_1$–C$_4$ alkyl), —CHO, or —COO(C$_1$–C$_4$ alkyl);

R$_5$ is phenyl, naphthyl, thienyl, benzothienyl, pyridyl, pyrimidyl, benzofuranyl, pyrazinyl or benzothiazolyl, wherein each one of said groups R$_5$ may optionally be substituted with from one to three substituents independently selected from fluoro, chloro, C₁–C₆ alkyl and C₁–C₆ alkoxy, or by one substituent selected from iodo, hydroxy, bromo, formyl, cyano, nitro, amino, trifluoromethyl, —NH(C₁–C₄ alkyl), —N(C₁–C₆)(C₁–C₂ alkyl), —COO(C₁–C₄ alkyl), —CO(C₁–C₄ alkyl), —COOH, —SO₂NH(C₁–C₄ alkyl), —SO₂N(C₁–C₄ alkyl)(C₁–C₂ alkyl), —SO₂NH₂, —NHSO₂(C₁–C₄ alkyl), —S(C₁–C₁ alkyl) and —SO₂(C₁–C₆ alkyl), wherein each of said C₁–C₄ alkyl and C₁–C₆ alkyl moieties in the foregoing $R^5$ groups may optionally be substituted with one to three fluorine atoms;

$R_7$ is hydrogen, C₁–C₄ alkyl, fluoro, chloro, bromo, iodo, —O(C₁–C₄ alkyl), —CH₂O(C₁–C₂ alkyl), —CO(C₁–C₂ alkyl);

$R_{11}$ is hydrogen, hydroxy, fluoro, or methoxy; and $R_{12}$ is hydrogen or C₁–C₄ alkyl;

with the proviso that when A is N, then: (a) B is not unsubstituted alkyl; (b) $R_5$ is not unsubstituted phenyl or monosubstituted phenyl; and (c) $R_3$ is not unsubstituted alkyl;

or a pharmaceutically acceptable salt thereof.

2. A compound according to claim 1, wherein B is —NR₁R₂, —NHCHR₁R₂, —CR₁R₂R₁₁, or —OCHR₁R₂; $R_1$ is C₁–C₄ alkyl, which may optionally be substituted with one hydroxy, fluoro or C₁–C₂ alkoxy group; $R_2$ is benzyl or C₁–C₆ alkyl, wherein said C₁–C₆ aikyl or the phenyl moiety of said benzyl may optionally be substituted with fluoro, C₁–C₂ alkyl, or C₁–C₂ alkoxy; and $R_{11}$ is hydrogen or fluoro.

3. A compound according to claim 1, wherein $R_1$ is C₁–C₄ alkyl substituted with hydroxy.

4. A compound according to claim 1, wherein $R_1$ and $R_2$ each independently are C₁–C₄ alkyl which may optionally be substituted with fluoro, C₁–C₂ alkyl or C₁–C₂ alkoxy.

5. A compound according to claim 1, wherein B is —NR₁R₂, and wherein —NR₁R₂ form a thiazolidinyl ring, or B is —NHCHR₁R₂ or —OCHR₁R₂, wherein the CHR₁R₂ moiety of said —NHCHR₁R₂ or —OCHR₁R₂ forms a tetrahydrofuranyl or tetrahydrothienyl ring.

6. A compound according to claim 1, wherein $R_3$ is methyl, chloro, or methoxy.

7. A compound according to claim 1, wherein $R_4$ is hydrogen, methyl or chloro.

8. A compound according to claim 1, wherein: (a) $R_3$ is methyl, chloro, or methoxy; (b) $R_4$ is hydrogen, methyl, ethyl, or chloro, and (c) $R_5$ is phenyl substituted by two or three substituents independently selected from fluoro, chloro, bromo, iodo, C₁–C₄ alkoxy, trifluoromethyl, C₁–C₆ alkyl which may optionally be substituted by one of hydroxy, C₁–C₄ alkoxy and fluoro, —(C₁–C₄ alkylene)O(C₁–C₂ alkyl), C₁–C₃ hydroxyalkyl, hydroxy, formyl, —COO(C₁–C₂ alkyl), and —(C(O)(C₁–C₄ alkyl).

9. A compound according to claim 1, wherein $R_5$ is phenyl substituted with two or three substituents independently selected from fluoro, chloro, bromo, iodo, C₁–C₄ alkoxy, trifluoromethyl, C₁–C₆ alkyl which may be substituted by one of hydroxy, C₁–C₄, alkoxy and fluoro, —(C₁–C₄ alkylene)O(C₁–C₂ alkyl), C₁–C₃ hydroxyalkyl, hydroxy, formyl, COO(C₁–C₂ alkyl) and —C(O)(C₁–C₄ alkyl).

10. A compound according to claim 1, wherein said compound is butyl-[3,6-dimethyl-1-(2,4,6-trimethylphenyl)-1H-pyrazolo[3,4-b]pyridin-4-yl]-ethylamine;

[3,6-dimethyl-1-(2,4,6-trimethylphenyl)-1H-pyrazolo[3,4,b]pyridin-4-yl]-(1-methoxymethylpropyl)-amine;

4-(1-methoxymethylpropoxy)-3,6-dimethyl-1-(2,4,6-trimethylphenyl)-1H-pyrazolo[3,4-b]pyridine;

(1-ethylpropyl)-[3,5,6-trimethyl-1-(2,4,6trimethylphenyl)-1H-pyrazolo[3,4b]pyridin-4-yl]-amine;

or a pharmaceutically acceptable salt of one of the foregoing compounds.

11. A pharmaceutical composition for the treatment of a disorder the treatment of which is effected or facilitated by antagonizing CRF; comprising an amount of a compound according to claim 1 that is effective in the treatment of said disorder, and a pharmaceutically acceptable carrier.

12. A method for the treatment of a disorder the treatment of which is effected or facilitated by antagonizing CRF; comprising administering to a subject in need of said treatment an amount of a compound according to claim 1 that is effective in treating such disorder.

13. A compound of the formula

II

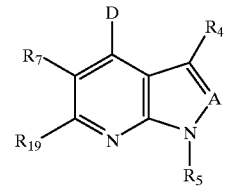

wherein A is N or —CR₆;

D is chloro, hydroxy or cyano;

$R_{19}$ is methyl, ethyl or chloro;

$R_3$ is C₁–C₄ alkyl, fluoro, chloro, bromo, iodo, —CH₂OH, —CH₂OCH₃, —O(C₁–C₃ alkyl), —S(C₁–C₃ alkyl), or —SO₂(C₁–C₃ alkyl);

$R_4$ is hydrogen, C₁–C₆ alkyl, fluoro, chloro, bromo, iodo, C₁–C₄ alkoxy, amino, —NHCH₃, —N(CH₃)₂, —CH₂OH, —CH₂OCH₃, or —SO$_n$(C₁–C₄ alkyl), wherein n is 0, 1 or 2, cyano, hydroxy, —CO(C₁–C₄ alkyl), —CHO, or —COO(C₁–C₄ alkyl);

$R_5$ is phenyl, naphthyl, thienyl, benzothienyl, pyridyl, pyrimidyl, benzofuranyl, pyrazinyl or benzothiazolyl, wherein each one of said groups $R_5$ may optionally be substituted with from one to three substituents independently selected from fluoro, chloro, C₁–C₆ alkyl and C₁–C₆ alkoxy, or by one substituent selected from iodo, hydroxy, bromo, formyl, cyano, nitro, amino, trifluoromethyl, —NH(C₁–C₄ alkyl), —N(C₁–C₆)(C₁–C₂ alkyl), —COO(C₁–C₄ alkyl), —CO(C₁–C₄ alkyl), —COOH, —SO₂NH(C₁–C₄ alkyl), —SO₂N(C₁–C₄ alkyl)(C₁–C₂ alkyl), —SO₂NH₂, —NHSO₂(C₁–C₄ alkyl), —S(C₁–C₆ alkyl) and —SO₂(C₁–C₆ alkyl), wherein each of said C₁–C₄ alkyl and C₁–C₆ alkyl moieties in the foregoing $R^5$ groups may optionally be substituted with one to three fluorine atoms;

$R_6$ is hydrogen, C₁–C₄ alkyl, fluoro, chloro, bromo, iodo, —CH₂OH, —CH₂OCH₃, or C₁–C₄ alkoxy; and $R_7$ is hydrogen, C₁–C₄ alkyl, fluoro, chloro, bromo, iodo, —O(C₁–C₄ alkyl), cyano, —CH₂OH, —CH₂O(C₁–C₂ alkyl), —CO(C₁–C₂ alkyl), or —COO(C₁–C₂ alkyl);

with the proviso that when A is N, $R_5$ is not unsubstituted phenyl and $R_{19}$ is not methyl or ethyl.

* * * * *